United States Patent
Verpoort et al.

(10) Patent No.: US 7,140,497 B2
(45) Date of Patent: Nov. 28, 2006

(54) SELECTIVE DELEUKOCYTATION UNIT FOR A PLATELET PRODUCT

(75) Inventors: Thierry Verpoort, Mouvaux (FR); Stéphane Chollet, Mouvaux (FR)

(73) Assignee: MacoPharma, Mouvaux (FR)

( * ) Notice: Subject to any disclaimer, the term of this patent is extended or adjusted under 35 U.S.C. 154(b) by 225 days.

(21) Appl. No.: 10/616,368

(22) Filed: Jul. 9, 2003

(65) Prior Publication Data
US 2004/0007540 A1     Jan. 15, 2004

(30) Foreign Application Priority Data
Jul. 10, 2002   (FR) .................................. 02 08687

(51) Int. Cl.
| | |
|---|---|
| *B01D 39/08* | (2006.01) |
| *B01D 39/16* | (2006.01) |
| *B01D 63/08* | (2006.01) |
| *B01D 61/00* | (2006.01) |
| *B01D 61/14* | (2006.01) |

(52) U.S. Cl. .............. 210/507; 210/500.1; 210/500.21; 210/500.27; 210/503; 210/645

(58) Field of Classification Search ................ 210/645, 210/500.1, 500.21, 500.22, 500.27, 503, 210/507, 510.1
See application file for complete search history.

(56) References Cited

U.S. PATENT DOCUMENTS

| | | | | |
|---|---|---|---|---|
| 4,927,676 A | | 5/1990 | Williams ..................... | 428/36 |
| 5,498,336 A | * | 3/1996 | Katsurada et al. .......... | 210/496 |
| 5,707,520 A | * | 1/1998 | Kuroki et al. ............... | 210/436 |
| 5,820,755 A | * | 10/1998 | Kraus et al. ................. | 210/483 |

FOREIGN PATENT DOCUMENTS

| | | |
|---|---|---|
| EP | 0526678 A1 | 2/1993 |
| FR | 2821762 | 9/2002 |
| JP | 2000135422 | 5/2000 |
| WO | 93/04763 | 3/1993 |
| WO | 94/17904 | 8/1994 |

OTHER PUBLICATIONS

"Adsorption of blood proteins on glow-discharge-modified polyurethane membranes", Kayirhan, et al, Journal of Appl. Polym. Sci., (81) pp. 1322-1332, Aug. 2001.*

* cited by examiner

*Primary Examiner*—Krishnan S. Menon
(74) *Attorney, Agent, or Firm*—Baker Botts L.L.P.

(57) ABSTRACT

The invention includes a filtration unit for the selective deleukocytation of a fluid containing blood platelets such as blood or a blood component. The unit includes a medium for deleukocytation by adsorption and/or filtration of the leukocytes. The medium is formed by at least one layer of non-woven polyurethane fabric which has been treated by gas plasma.

The invention also includes bag systems containing such a unit, including closed filtration systems.

14 Claims, 3 Drawing Sheets

SELECTIVE DELEUKOCYTATION UNIT FOR A PLATELET PRODUCT

PRIORITY CLAIM

The present application claims priority under § 119(d) French Application No. FR 02/08687 filed Jul. 10, 2002.

FIELD OF THE INVENTION

The invention concerns a filtration unit for the selective deleukocytation of a fluid containing blood platelets. Specifically it may apply to the filtration of blood or a blood component containing platelets such as a platelet-rich plasma (PRP) or a platelet concentrate (PC) as well as to the separation and collection of the blood components. The invention also includes bag systems comprising such a filtration unit in particular in a closed circuit.

BACKGROUND OF THE INVENTION

Whole blood is a tissue with two components: the blood cells (red corpuscles, leukocytes and platelets), and plasma, a pale yellow liquid in which the blood cells are in suspension.

At the present time, patients are given transfusions only of the blood components necessary for their condition. For example, only platelet concentrates are transfused to patients suffering from thrombocytopenia, that is to say those whose platelet content in the blood is reduced.

Blood components are normally separated by two types of centrifugation. "Soft" centrifugation of the whole blood results in separation into two layers: a bottom layer with a high red corpuscle content known as a red corpuscle concentrate (RCC); and a top layer containing the plasma, platelets and leukocytes, referred to as a platelet-rich plasma (PRP). "Hard" centrifugation results in a separation into three layers: a bottom layer of RCC; a top layer of plasma with a low platelet content; and an intermediate layer formed essentially of leukocytes and platelets, referred to as a leukocyte-platelet layer or buffy coat. The platelet concentrate (PC) is obtained by centrifugation of the PRP or the buffy coat.

The presence of leukocytes in blood components intended for transfusion has very significant undesirable effects. Leukocytes increase the risks of immune rejection such as GVHD (Graft Versus Host Disease: rejection of the graft by the host) and assist in the transmission of infectious agents. Leukocytes also negatively affect the preservation of platelets. Therefore, it is desirable to remove leukocytes from blood or blood components. Filtration units with a medium for deleukocytation of the whole blood and/or each of the blood components have been developed. However, the majority of these media retain the not only leukocytes but also the platelets so that they do not make it possible to obtain a platelet filtrate product free from leukocytes.

To allow the selective elimination of the leukocytes and the passage of platelets, several chemical and/or physical treatments of known filtering media have been proposed.

For example, it has been envisaged treating the filtering medium by coating or radiation grafting of various chemical substances may limit the adhesion of the platelets to the filtering medium. These treatments have the drawback of using organic reagents which may be found in the leukodepleted blood or blood component.

In addition, it has been envisaged, for example in WO-93/04763, to treat the filtration medium by gas plasma so as to reduce the retention of the platelets. However, to be effective, this type of treatment may require operating conditions, particularly in terms of time, which are constraining.

SUMMARY OF THE INVENTION

The present invention includes a deleukocytation medium formed by a material with intrinsic non-retention of the blood platelets. The material may be in the form of at least one non-woven layer so as to improve its capacity for elimination of leukocytes. The medium may be treated by gas plasma so as to improve its hydrophilicity.

In particular, the invention includes a filtration unit incorporating such a deleukocytation medium. Use of the unit may result in a loss of less than 20% of platelets and a degree of deleukocytation greater than 2 log.

In addition, the filtration unit may be incorporated in bag systems allowing the filtration of fluids containing platelets and possibly separation of the various blood components in closed circuit.

Specifically, an embodiment of the invention includes a filtration unit for the selective deleukocytation of a fluid containing blood platelets such as blood or a blood component. The unit includes an external enclosure provided with at least one inlet orifice and at least one outlet orifice. The enclosure encloses a porous element including a medium for deleukocytation by adsorption and/or filtration of leukocytes. The medium may be formed by at least one non-woven layer including polyurethane which has been treated by gas plasma.

According to a more specific embodiment, the deleukocytation medium also includes at least one membrane placed downstream of the medium.

In another specific embodiment, the invention includes a bag system for the selective deleukocytation of a fluid containing blood platelets. The system may include a collection bag intended to receive the fluid to be filtered. The bag may be connected, by means of a tube at its outlet orifice, to an inlet orifice of a filtration unit according to the invention. A filtrate collection bag may be connected to an outlet by means of a tube and at the filtrate collection bag's inlet orifice.

According to a particular embodiment, the bag system may be used to collect and filter a fluid containing platelets, in particular a set of buffy coats or platelet concentrates.

According to another particular embodiment, the bag system may be used for the separation of blood components from whole blood and for the filtration of a fluid containing platelets, in particular PRP, in closed circuit.

Another embodiment of the invention relates to a polyurethane filtration material treated by gas plasma and methods of producing such material. The material in more specific embodiments may be formed into a non-woven, porous fabric.

The above summary presents only brief descriptions of certain embodiments of the invention. For a more complete understanding of additional embodiments of the invention, reference may be had to the following drawings and detailed description, in which like components are designated by like numbers.

DETAILED DESCRIPTION

Figure 1:
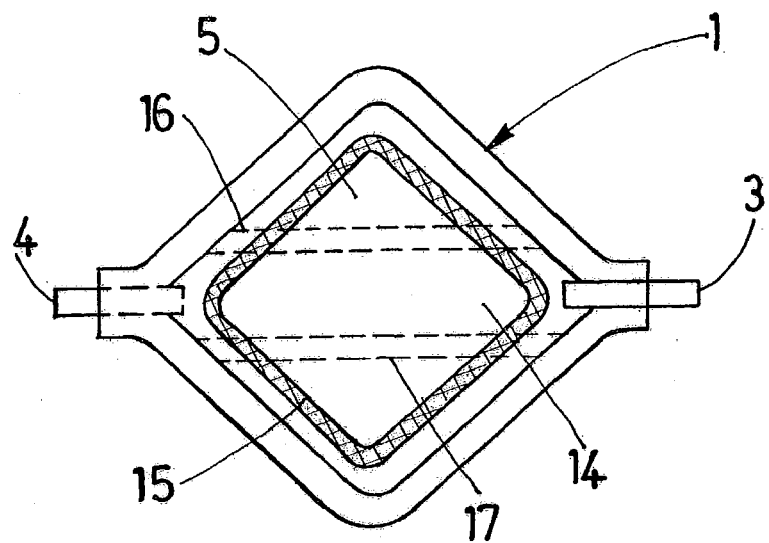
FIG. 1 depicts in front view a filtration unit according to one embodiment of the invention.
Figure 2:
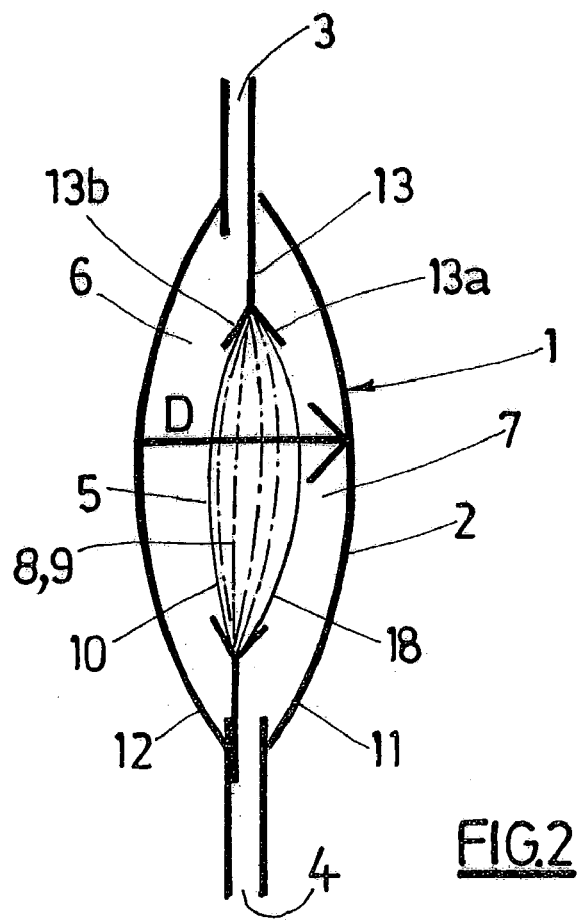
FIG. 2 depicts schematically and in longitudinal section the filtration unit of FIG. 1.

FIGS. 1 and 2 depict an embodiment of the invention in which filtration unit 1 is operable to allow the selective deleukocytation of a fluid containing platelets and the recovery of the platelets from the filtered fluid.

A fluid containing platelets may for example be whole blood, platelet-rich plasma (PRP), buffy coat or platelet concentrate.

In particular, the filtration unit 1 is operable to filter a PRP unit, (the quantity of PRP obtained after centrifugation of one donated unit of whole blood). The filtration unit can also serve to filter a set of buffy coats or platelet concentrates (PC), (normally the quantity of buffy coats or PC obtained after combining two to eight units of buffy coats or PC, where one unit is obtained from one donated unit of whole blood).

In the embodiment depicted in FIGS. 1 and 2, the filtration unit 1 includes an external enclosure 2 provided with an inlet orifice 3 operable to receive the fluid to be filtered and an outlet orifice 4 operable to collect the filtrate, between which the fluid flows in a direction D.

The filtration unit 1 also includes a porous element 5 disposed in the external enclosure 2 so as to delimit an inlet compartment 6 in communication with the inlet orifice 3 and an outlet compartment 7 in communication with the outlet orifice 4.

In this application, the terms "upstream" and "downstream" refer to the direction of flow of the fluid in the filtration unit 1 as indicated by direction D.

The porous element 5 includes a deleukocytation medium 8 capable of eliminating, by adsorption and/or filtration, the leukocytes present in a platelet product. The deleukocytation medium 8 is capable of allowing the platelets to pass, that is to say the platelets do not substantially adhere to the surface of the deleukocytation medium 8.

The deleukocytation medium 8 may be multilayer, including several layers 9. According to one embodiment, the layers 9 have a mean pore diameter which decreases in the direction of flow D so as to create porosity gradient.

This porosity gradient improves the retention capacity for the leukocytes present in the fluid containing platelets while preventing blocking or clogging of the deleukocytation medium 8.

The porosity gradient may vary between 3 and 15 µm, continuously or discretely.

The filtration surface of the porous element 5 depends on the quantity of fluid containing platelets to be filtered and the type of filtration used. In specific embodiments filtration may be by gravity or under pressure. When the fluid to be filtered is a PRP, the filtration surface of the filter may be for example between 15 and 58 cm$^2$, in particular 55 cm$^2$. When the fluid to be filtered includes one to four units of platelet concentrates, the filtration surface may be between 15 and 35 cm$^2$, in particular 20 cm$^2$.

The deleukocytation medium 8 includes at least one layer formed by a non-woven material based on polyurethane.

Non-woven layers of polyurethane contained in the filtration unit 1 preferably have sufficient biocompatibility for the platelets not to adhere to them, and while exhibiting an improved leukocyte retention capacity.

The non-woven layers of polyurethane may be treated by gas plasma before introduction into the filtration unit 1. This treatment increases the hydrophilicity of the medium and therefore allows initiation of filtration by simple gravity without requiring pressurized filtration. However, pressurized filtration may still be used, for example to increase the filtration rate while limiting the loss of volume.

The use of a polymeric or copolymeric cladding or radiation/grafting of a polymer or copolymer in order to prevent the platelets adhering to the non-woven layers of polyurethane is therefore not necessary in the present invention.

The mean diameter of the pores of a polyurethane non-woven fabric may be between 5 and 15 µm, in particular 7 and 15 µm. The polyurethane non-woven fabric may undergo a compression of the calendering type in order to control the size of its pores.

According to another embodiment, the deleukocytation medium 8 also includes at least one membrane capable of retaining leukocytes and allowing platelets to pass. For example, the membrane may be produced from a material chosen from polymers of fluorocarbon polymers such as PVDF, celluloses, polyurethanes, polysulphones, sulphonated polyethers, polycarbonate and in particular polyvinylpyrrolidone/polysulphone (PVP/PSU) copolymer.

In a more specific embodiment, the PVP/PSU copolymer is approximately 5% PVP and 95% PSU.

The diameter of the pores of the membrane may vary from 2 to 10 µm. The membrane is placed downstream of the layers of non-woven polyurethane.

The nature and the physico-chemical properties of the membrane used may be such that the membrane requires no chemical and/or physical treatment in order to increase its hydrophilicity. The membrane provides a so-called screen filtration; its pores are calibrated to allow the platelets to pass while retaining the leukocytes.

In the particular embodiment depicted in FIGS. 1 and 2, the external enclosure 2 is flexible and formed by the assembly of two sheets 11, 12 of flexible plastic material mutually connected together, for example by welding at their periphery.

The porous element 5 is maintained in the external enclosure 2 by a deformable sealed association which is formed by a flexible frame 13.

The flexible frame 13 is formed by an assembly of two sheets 13a and 13b, for example plasticized, between which the porous element 5 is placed.

These two sheets 13a, 13b are perforated in their central part and each comprise at least one opening 14 enabling the fluid to be filtered to pass.

The two sheets 13a, 13b are fixed together preferably at the periphery of the porous element 5, for example by a welding bead 15, implemented through the porous element 5, providing both the fixing of the porous element 5 and also impermeability.

The welding of the sheets 13a, 13b through the porous element 5 causes a compression, forming a sealed bead around the porous element 5.

The flexible frame 13 is welded at its periphery with the sheets 11 and 12 forming the external enclosure 2 mutually over their entire circumference and at their periphery, thus providing impermeability.

At the time of this welding, the inlet orifice 3, formed by a portion of tube, is disposed on one side of the flexible frame 13 and the outlet orifice 4, formed by another portion of tube, is disposed on the other side of the flexible frame 13.

To prevent the porous element sticking against the external enclosure 2 and thus interfering with the flow of fluid, two separation rings 16, 17 are placed inside the outlet compartment 7, between the porous element 5 and the external enclosure 2.

The rings may be produced from flexible tubes welded for example at the internal wall of the sheet of the external enclosure 2, for example at the peripheral weld.

The number of separation rings 16, 17 may vary according to, for example the dimensions of the filtration unit 1.

In another embodiment (not shown), the external enclosure is rigid. For example it may be produced from rigid plastics material such as polycarbonate.

As described above in relation to FIGS. 1 and 2, the porous element 5 is held in a flexible frame 13 by a welding bead 15. To allow welding of the porous element with the sheets 13a, 13b forming the flexible frame 13, the materials of the porous element in contact with the flexible frame 13 must be weldable.

The porous element 5 may include a prefilter 10 upstream of the deleukocytation medium 8 in order to eliminate the gel or microaggregate particles and large leukocytes, and to prevent clogging of the deleukocytation medium 8. In addition, it may also include a post-filter 18 provided downstream of the deleukocytation medium 8.

The prefilter 10 and/or the post-filter 18 may be formed by a material chosen from polyester, polypropylene, polyethylene or polyurethane, in the form of a woven fabric, a knitted fabric or a non-woven fabric, with a pore size sufficient to prevent the retention of the platelets.

Figure 3:
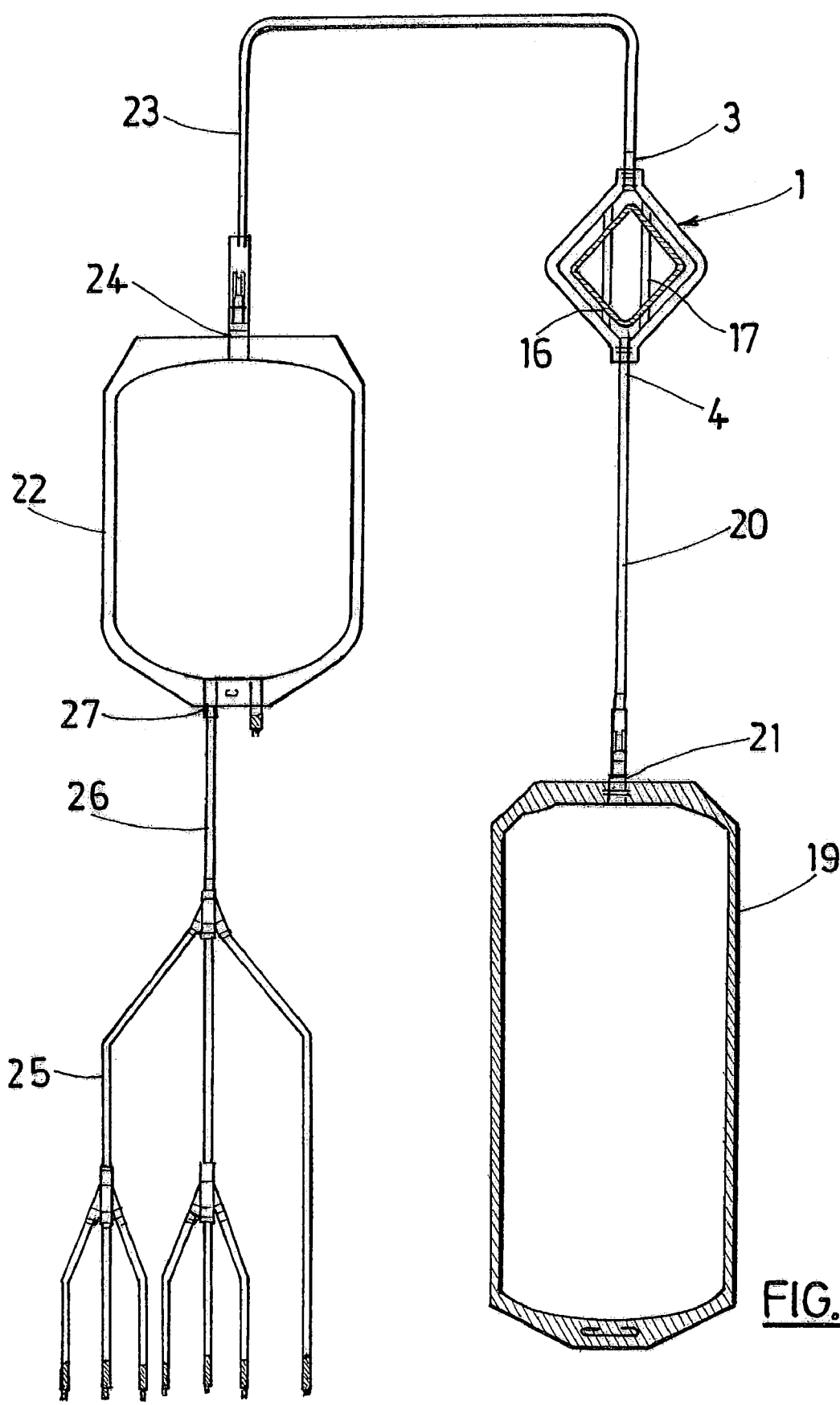
FIG. 3 depicts in schematic view a bag system for the selective deleukocytation of a fluid containing platelets according to one embodiment of the invention.
Figure 4:
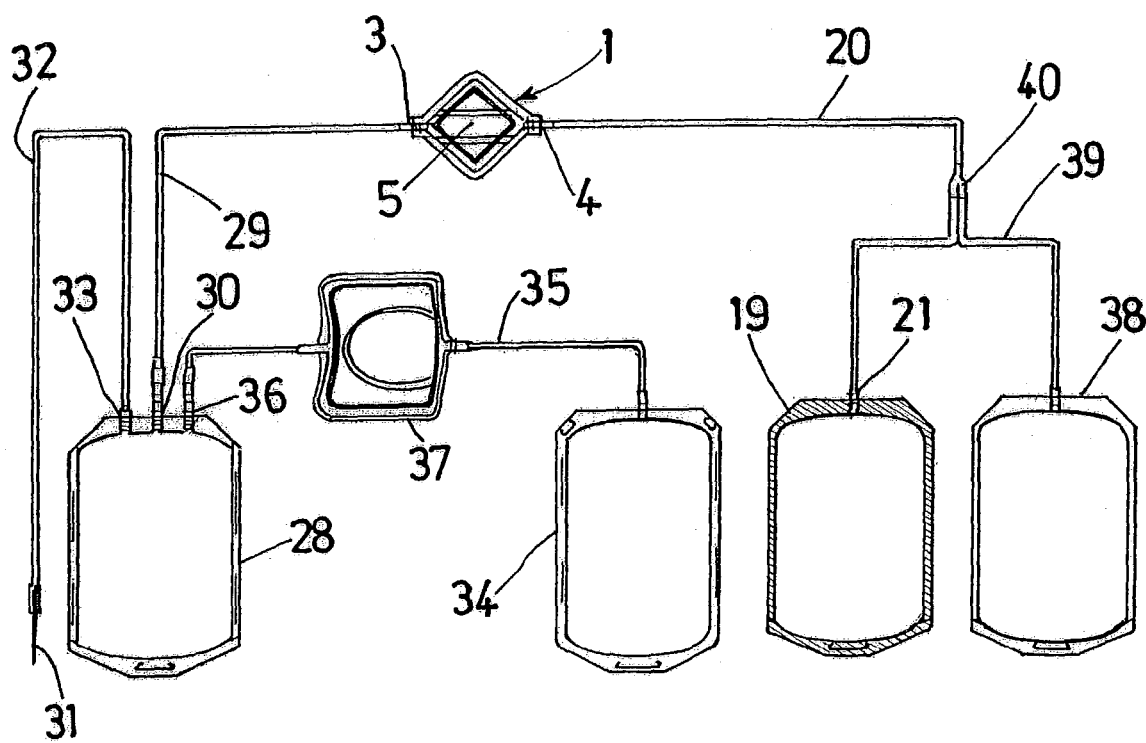
FIG. 4 depicts in schematic view a bag system for the separation of blood components and the selective deleukocytation of a fluid containing platelets according to one embodiment of the invention.

FIGS. 3 and 4 depict two embodiments of a bag system for the deleukocytation of a fluid containing platelets. The system includes a bag 19 to collect the filtrate, connected at the inlet orifice 21 of the said bag 19 by a first tube 20 to an outlet orifice 4 of the filtration unit.

The bag 19 to collect the filtrate may be flexible and includes a biocompatible material having a permeability sufficient to keep the platelets viable during their storage. The bag 19 may be produced in particular from PVC plasticized by means of tri 2-ethylhexyl trimellitate or from ethylene vinyl acetate (EVA).

The tubes may be flexible, weldable and able to be cut and the connections between the various elements of the bag systems may be fixed and sealed.

In relation to FIG. 3, for filtration of a set of buffy coats, or respectively of platelet concentrates through filtration unit 1 a bag 22 to contain the fluid to be filtered is connected at the outlet orifice 24 by means of a second tube 23 to an inlet orifice 3 of the filtration unit 1.

The system also includes connection means 25 connected, by a third tube 26, to an inlet orifice 27 of the bag 22 to contain the fluid to be filtered.

The connection means 25 is intended to connect one or more bags (not shown) containing units of buffy coats or platelet concentrates, and possibly one or more bags containing a platelet storage solution.

Suitable platelet storage solutions are available on the market. One particular platelet storage solution comprises 2.94 g of sodium citrate $2H_2O$, 4.08 g of sodium acetate $3H_2O$, 6.75 g of sodium chloride in 100 ml of water for injection, at a pH of 7.2.

The connection means may, for example, be perforators or spring rings for sterile connection.

In a particular embodiment of the system depicted in FIG. 3, seven bags each containing a unit of buffy coat, are placed in fluid communication by connection means 25, with the bag 22 to contain the fluid to be filtered. The bag system is then placed in a centrifuge so that the outlet orifice 24 of the bag 22 is directed upwards. The bag 22 is then centrifuged so as to obtain platelets in the supernatant and the leukocytes and red corpuscles in the remainder. The supernatant is sent through the outlet orifice 24 of bag 22 through to the bag 19 to receive the filtrate from the filtration unit 1. In this way deleukocyted platelet concentrates are recovered in the filtrate collection bag 19.

In another particular embodiment of the system depicted in FIG. 3, six bags each containing a unit of platelet concentrate and a seventh bag containing a platelet storage solution are placed in fluid communication by connection means 25, with the bag 22 to contain the fluid to be filtered. The mixture of platelet concentrates and platelet storage solution is then sent through the outlet orifice 24 of bag 22 through to bag 19 to receive the filtrate from the filtration unit 1. In this way deleukocyted platelet concentrates are recovered in the filtrate collection bag 19.

In another embodiment (not shown), the connection means 25 may be directly connected by the second tube 23 to the inlet orifice 3 of the filtration unit 1. In this case, platelet concentrates obtained by buffy coat centrifugation may be directly connected.

FIG. 4 depicts another embodiment of a bag system according to the invention for the separation of blood components and the deleukocytation of a PRP in closed circuit.

In addition to the filtration unit and the bag 19 to collect the filtrate, the bag system includes a collection bag 28 containing an ACD or CPD anticoagulant and connected by a fourth tube 29 to the outlet orifice 30 of the filtration unit 1 and a blood sampling device 31 connected by a fifth tube 32 to an inlet orifice 33 of the collection bag 28.

In addition, the system includes at least one satellite bag 34 containing a solution for preserving red corpuscles such as SAGM and connected by a sixth tube 35 to a second outlet orifice 36 of the collection bag 22.

The tube 35 may include a filtration unit 37 to eliminate the leukocytes from the red corpuscles.

If necessary, a plasma collection bag 38 may be in fluid communication with the filtrate collection bag 19, by a seventh tube 39 through a connector 40 to the first tube 20.

In a particular embodiment, not shown, the system also includes a bag containing a platelet preservation solution in fluid communication with the filtrate collection bag 19.

Using a particular embodiment of the invention as shown in FIG. 4, whole blood may be removed by the removal device 31 in the collection bag 28. The system overall is then centrifuged so as to obtain in the collection bag 28 a bottom layer of red corpuscle concentrate and a top layer of PRP. The PRP is sent into the filtrate collection bag 19 by way of the filtration unit 1. The red corpuscle concentrate remaining in the collection bag 28 is sent into the satellite bag 34 by way of the filter 37 for deleukocyting the red corpuscles. The tube 20 may then be sealed and cut in order to separate the filtrate collection bag 19 and plasma collection bag 38 from the rest of the system. After centrifugation of the filtered PRP, a top layer of plasma is obtained which is sent into the collection bag 38. The bottom layer is platelet concentrate.

The following examples are provided to further illustrate specific aspects of the invention.

EXAMPLE 1

A filtration unit 1 as depicted in FIGS. 1 and 2 with a porous element 5 includes:
one polyester non-woven layer having a mean porosity of 35 μm,
four polyurethane non-woven layers with an average pore size of 13.6 μm,
five layers of PVP/PSU membrane with an average porosity of between 4.5 μm and 5.5 μm, and
one polyester non-woven layer having an average porosity of 35 tm.

The polyurethane non-woven fabric was treated with gas plasma layer by layer under the following operating conditions:
Power: 1000 watts;
Radio frequency: 13.56 MHz;
Treatment time: 30 seconds;
Pressure: 200 to 220 millitorre;
$O_2$ flow rate: 1 to 2 liters per minute.
The filtration surface was 20 cm².

A set of platelet concentrates was formed in the bag 22 of a bag system as depicted in FIG. 3, and then the set was passed into the filtration unit 1 described above.

The platelet loss measured was less than 15% and the degree of leukocyte depletion is greater than 2 log.

EXAMPLE 2

A filtration unit 1 as depicted in FIGS. 1 and 2 with a porous element 5 includes:
one layer of polyester non-woven fabric having an average porosity of 35 μm,
ten layers of polyurethane non-woven fabric with an average pore size of 8 μm,
one layer of polyester non-woven fabric having an average porosity of 35 μm.

The plasma treatment was carried out under the same operating conditions as in Example 1 and the results obtained were similar.

The above description illustrates specific aspects of certain embodiments of the invention. Variations will be apparent to one skilled in the art are intended to be encompassed with the invention.

What is claimed is:

1. A fluid filter material comprising an oxygen gas plasma-treated polyurethane non-woven porous fabric layer having a mean pore diameter between 5 and 15 μm, wherein the polyurethane is not further modified by radiation/graft polymerization after oxygen plasma treatment, and wherein the filter shows greater than 2 log reduction of leukocytes and less than 15% reduction of platelets.

2. The filter material of claim 1, wherein the oxygen gas plasma-treated polyurethane is more hydrophilic than untreated polyurethane.

3. The filter material of claim 1, wherein the fabric is operable to selectively leukodeplete a fluid containing platelets when the fluid flows through the fabric.

4. The filter material of claim 1, wherein platelets do not substantially adhere to the oxygen gas plasma-treated fabric.

5. The filter material of claim 1, wherein the mean diameter of the pores is approximately 13 μm.

6. The filter material of claim 1, wherein the mean diameter of the pores is approximately 8 μm.

7. A fluid filter material comprising an oxygen gas plasma-treated polyurethane non-woven porous fabric layer having a mean pore diameter between 5 and 15 μm, wherein the oxygen gas plasma-treated polyurethane is more hydrophilic than untreated polyurethane, and wherein the polyurethane is not further modified by radiation/graft polymerization after oxygen plasma treatment, and wherein the filter shows greater than 2 log reduction of leukocytes and less than 15% reduction of platelets.

8. The filter material of claim 7, wherein the fabric is operable to selectively leukodeplete a fluid containing platelets when the fluid flows through the fabric.

9. The filter material of claim 7, wherein platelets do not substantially adhere to the oxygen gas plasma-treated fabric.

10. The filter material of claim 7, wherein a mean diameter of the pores is large enough to allow passage of substantially all platelets in a fluid, but small enough to prevent passage of leukocytes in the fluid.

11. The filter material of claim 7, wherein the mean diameter of the pores is approximately 13 μm.

12. The filter material of claim 7, wherein the mean diameter of the pores is approximately 8 μm.

13. A fluid filter material comprising an oxygen gas plasma-treated polyurethane non-woven porous fabric layer having a mean pore diameter between 5 and 15 μm, wherein the oxygen gas plasma-treated polyurethane is more hydrophilic than untreated polyurethane, wherein the fabric is operable to selectively leukodeplete a fluid containing platelets when the fluid flows through the fabric, wherein platelets do not substantially adhere to the oxygen gas plasma-treated fabric, and wherein the polyurethane is not further modified by radiation/graft polymerization after oxygen plasma treatment, and wherein the filter shows greater than 2 log reduction of leukocytes and less than 15% reduction of platelets.

14. A fluid filter material comprising an oxygen gas plasma-treated polyurethane non-woven porous fabric layer having a mean pore diameter between 5 and 15 μm, wherein the oxygen gas plasma-treated polyurethane is more hydrophilic than untreated polyurethane, wherein the fabric is operable to selectively leukodeplete a fluid containing platelets when the fluid flows through the fabric, wherein platelets do not substantially adhere to the oxygen gas plasma-treated fabric, wherein the oxygen gas plasma-treated fabric comprises pores having a mean diameter of large enough to allow passage of substantially all platelets in a fluid, but small enough to prevent passage of leukocytes in the fluid, and wherein the polyurethane is not further modified by radiation/graft polymerization after oxygen plasma treatment, and wherein the filter shows greater than 2 log reduction of leukocytes and less than 15% reduction of platelets.

* * * * *